United States Patent [19]
Seto et al.

[11] Patent Number: 5,617,973
[45] Date of Patent: Apr. 8, 1997

[54] CARTRIDGE FOR DRY-TYPE CHEMICAL ANALYSIS FILMS

[75] Inventors: Yoshihiro Seto; Fumio Sugaya, both of Kanagawa-ken, Japan

[73] Assignee: Fuji Photo Film Co., Ltd., Kanagawa, Japan

[21] Appl. No.: 405,808

[22] Filed: Mar. 16, 1995

[30] Foreign Application Priority Data

Apr. 15, 1994 [JP] Japan .................................. 6-077221

[51] Int. Cl.$^6$ ........................................................ B65H 1/08
[52] U.S. Cl. ............................ 221/56; 221/58; 221/59; 221/279; 221/281; 221/303
[58] Field of Search ............................... 221/226, 279, 221/281, 303, 56, 59, 58

[56] References Cited

U.S. PATENT DOCUMENTS

| | | | |
|---|---|---|---|
| 2,426,995 | 9/1947 | Gibbs | 221/279 X |
| 2,620,061 | 12/1952 | Uxa | 221/281 X |
| 3,370,748 | 2/1968 | Koerper | 221/59 |
| 3,393,831 | 7/1968 | Stewart | 221/232 |
| 3,397,818 | 8/1968 | Rey | 221/232 |
| 4,005,801 | 2/1977 | Musser | 221/56 |
| 4,151,931 | 5/1979 | Scherer et al. | 221/226 |
| 5,080,258 | 1/1992 | Hinterreiter | 221/279 X |
| 5,388,724 | 2/1995 | Adams et al. | 221/279 X |

FOREIGN PATENT DOCUMENTS

| | | | |
|---|---|---|---|
| 0304838A2 | 8/1988 | European Pat. Off. | B01L 11/00 |
| 220053 | 6/1942 | Switzerland | 118/56 |
| 278812 | 10/1951 | Switzerland | 221/281 X |

*Primary Examiner*—William E. Terrell
*Assistant Examiner*—Khoi H. Tran
*Attorney, Agent, or Firm*—Sughrue, Mion, Zinn, Macpeak & Seas

[57] ABSTRACT

A cartridge for dry-type chemical analysis films comprises a box housing, which accommodates therein a stack of dry-type chemical analysis films and which has a take-out opening at one end such that the dry-type chemical analysis films may be taken out of the box housing through the take-out opening one after another. A push member is located in the box housing so as to be capable of sliding. The push member comes into contact with the stack of the dry-type chemical analysis films from the side opposite to the take-out opening and pushes the stack of the dry-type chemical analysis films in the direction heading towards the take-out opening. An urging member is located in the box housing and urges the push member in the direction heading towards the take-out opening. A restriction member is located in the box housing and restricts the distance of movement of the push member in the direction heading away from the take-out opening to at most a value equal to the width of each dry-type chemical analysis film.

4 Claims, 4 Drawing Sheets

CARTRIDGE FOR DRY-TYPE CHEMICAL ANALYSIS FILMS

BACKGROUND OF THE INVENTION

1. Field of the Invention

This invention relates to a cartridge for accommodating therein dry-type chemical analysis films each having a layer containing a reagent, which will undergo a chemical reaction, a biochemical reaction, an immune reaction, or the like, with a specific biochemical substance contained in a liquid sample, such as blood or urine, and will thereby give rise to a change in optical density, such that the dry-type chemical analysis films can be taken out of a take-out opening one after another.

2. Description of the Prior Art

Recently, dry-type integral multi-layer chemical analysis films (also referred to as multi-layer chemical analysis elements) were developed for use in systems designed for performing quantitative analyses, with which systems the amounts or activity values of specific chemical constituents contained in droplets of liquid samples spotted onto the dry-type chemical analysis films or the amounts of specific physical constituents contained in the droplets of the liquid samples, are determined. Also, filter paper type of test pieces have been proposed, and single-layer or multi-layer test pieces have been obtained by improving the filter paper type of test pieces. Some of them have been used in practice.

In order to use a dry-type chemical analysis film in the quantitative analysis of a chemical constituent, or the like, contained in a liquid sample, a droplet of the liquid sample is put on the dry-type chemical analysis film. Specifically, in cases where the dry-type chemical analysis film has a spreading layer, the droplet of the liquid sample is put on the spreading layer of the dry-type chemical analysis film. In cases where the dry-type chemical analysis film has no spreading layer, the droplet of the liquid sample is put directly on the reagent layer of the dry-type chemical analysis film. The liquid sample is then kept at a predetermined temperature (i.e., incubated) for a predetermined time in an incubator, which causes a color reaction (i.e., a coloring matter generating reaction or a discoloration reaction of an indicator dye). The dry-type chemical analysis film is then exposed to light having a wavelength, which is selected in advance. The selection of the wavelength depends on the specific biochemical substances contained in the liquid sample and the constituents of a reagent contained in the dry-type chemical analysis film. Light is thus irradiated to the dry-type chemical analysis film, and the optical density is determined. The optical density depends on how much of a reaction product was formed by the reaction between the liquid sample and the reagent in the dry-type chemical analysis film. Thereafter, a calibration curve, which is created in advance and which represents the relationship between the optical densities and the concentrations of the specific biochemical substance in liquid samples, is used in order to determine the concentration (i.e., the content) or the activity value of the biochemical substance in the liquid sample from the optical density, which has been determined.

The dry-type integral multi-layer chemical analysis film described above comprises a substrate, which is constituted of an organic polymer, and at least a single reagent layer containing a reagent. The dry-type integral multi-layer chemical analysis film should preferably be provided with a spreading layer, which is overlaid upon the reagent layer.

The dry-type integral multi-layer chemical analysis film is formed as a dry-type chemical analysis film piece having a predetermined shape, e.g., a square shape or a rectangular shape. Such that the operations using the dry-type chemical analysis film pieces may be carried out automatically, each of the dry-type chemical analysis film pieces takes on the form of a chemical analysis slide, which comprises organic polymer frames and the dry-type chemical analysis film piece sandwiched between the frames. Also, the inventors proposed a technique for loading a plurality of dry-type frameless chemical analysis film pieces directly into a cartridge, accommodating the cartridge in a film feeding device in a biochemical analysis system, taking the dry-type frameless chemical analysis film pieces out of the film feeding device one after another, and subjecting the dry-type frameless chemical analysis film pieces to a measurement one after another.

A technique for accommodating and feeding out dry-type chemical analysis films is disclosed in, for example, U.S. Pat. No. 4,151,931. With the disclosed technique, a plurality of dry-type chemical analysis films are stacked and accommodated in a cartridge having a take-out opening, which is formed at a top end of the cartridge and is open to a side surface of the cartridge. The dry-type chemical analysis film located at the top position is pushed out of the cartridge by a push-out blade, which is operated horizontally. In this manner, the dry-type chemical analysis film is fed into an analysis system. A support member for supporting the dry-type chemical analysis films is located at the bottom of the cartridge such that the support member can be moved only upwardly by a ratchet mechanism. The support member is moved upwardly by the operation of a plunger from below and is thus successively urged towards the take-out opening.

Also, a different technique for feeding out dry-type chemical analysis films is disclosed in, for example, U.S. patent application Ser. No. 08/253,607 and European Patent Publication No. 304,838. With the disclosed technique, dry-type chemical analysis films accommodated in a cartridge are pushed towards a take-out opening by a push member, which is urged by a spring (serving as an urging means). In this manner, the dry-type chemical analysis films are taken out of the take-out opening one after another.

However, when a cartridge, in which the dry-type chemical analysis films are stacked and accommodated, is stored or conveyed before being loaded into a biochemical analysis system, or when the cartridge is taken out of the biochemical analysis system and processed for maintenance, or the like, after being loaded into the biochemical analysis system, it often occurs that the cartridge falls and strikes against the floor, or the like, or is subjected to other impacts. In such cases, with the conventional cartridges described above, the problems occur in that the dry-type chemical analysis films accommodated in the cartridge are disturbed, turned over, or subjected to an excessive pushing force. As a result, adverse effects occur upon the operation for taking the dry-type chemical analysis film out of the cartridge and the measurement operation. In particular, the aforesaid problems occur markedly in cases where the cartridge accommodates therein a plurality of dry-type chemical analysis film pieces, which are curved and deformed and which exhibit a high resilience in the thickness direction when they are stacked.

Specifically, with the cartridge for dry-type chemical analysis films, wherein the urging of the push member provided with the ratchet mechanism is carried out by the insertion of the plunger, because of the ratchet mechanism, the push member can smoothly move in the direction, that pushes the dry-type chemical analysis films, but cannot move reversely. Therefore, in cases where the cartridge falls and strikes against the floor, or the like, with the side opposite to the take-out opening facing down, the push member does not move, and no problem occurs. However, in cases where the cartridge falls and strikes against the floor, or the like, with the side of the take-out opening facing down, the push member moves towards the take-out opening and locks the dry-type chemical analysis films in the pushed state. Therefore, there is the risk that the operation for taking the dry-type chemical analysis films out of the take-out opening one after another cannot be carried out smoothly due to the action of the excessive pushing force.

With the cartridge, wherein dry-type chemical analysis films are always pushed towards the take-out opening by the push member urged by the urging means, such as a spring, in cases where the cartridge falls and strikes against the floor, or the like, with the side of the take-out opening facing down, the push member moves in the direction, that compresses the dry-type chemical analysis films, and thereafter the push member returns to the original position. Therefore, in such cases, no problem occurs. However, in cases where the cartridge falls and strikes against the floor, or the like, with the side opposite to the take-out opening facing down, the push member moves in the direction heading away from the take-out opening due to deformation of the urging means, and the dry-type chemical analysis films are released from the pushing force. As a result, the dry-type chemical analysis films are disturbed. Also, if a space larger than the width of the dry-type chemical analysis films is formed, there is the risk that the dry-type chemical analysis films become upright or are turned over. In such cases, the dry-type chemical analysis films cannot be accurately taken out of the take-out opening one after another. Also, if the dry-type chemical analysis films, which have been turned over, are taken out and subjected to the operation for measurement, the measurement cannot be carried out.

SUMMARY OF THE INVENTION

The primary object of the present invention is to provide a cartridge for dry-type chemical analysis films, wherein the dry-type chemical analysis films accommodated in the cartridge are prevented from being turned over or compressed when the cartridge falls and strikes against the floor, or the like, or is subjected to other impacts.

Another object of the present invention is to provide a cartridge for dry-type chemical analysis films, wherein the dry-type chemical analysis films are capable of being accurately taken out of the cartridge one after another.

The present invention provides a cartridge for dry-type chemical analysis films, comprising:

i) a box housing, which accommodates therein a stack of a plurality of dry-type chemical analysis films and which has a take-out opening at one end such that the dry-type chemical analysis films may be taken out of the box housing through the take-out opening one after another, ii) a push member, which is located in the box housing so as to be capable of sliding, and which comes into contact with the stack of the plurality of the dry-type chemical analysis films from the side opposite to the take-out opening and pushes the stack of the plurality of the dry-type chemical analysis films in the direction heading towards the take-out opening, iii) an urging means, which is located in the box housing and which urges the push member in the direction heading towards the take-out opening, and iv) a restriction means, which is located in the box housing and which restricts the distance of movement of the push member in the direction heading away from the take-out opening to at most a value equal to the width of each dry-type chemical analysis film.

The present invention also provides a cartridge for dry-type chemical analysis films, comprising:

i) a box housing, which accommodates therein a stack of a plurality of dry-type chemical analysis films and which has a take-out opening at one end such that the dry-type chemical analysis films may be taken out of the box housing through the take-out opening one after another, ii) a push member, which is located in the box housing so as to be capable of sliding, and which comes into contact with the stack of the plurality of the dry-type chemical analysis films from the side opposite to the take-out opening and pushes the stack of the plurality of the dry-type chemical analysis films in the direction heading towards the take-out opening, iii) an urging means, which is located in the box housing and which urges the push member in the direction heading towards the take-out opening, and iv) a restriction means, which is located in the box housing and which restricts the distance of movement of the push member in the direction heading away from the take-out opening to at most a value equal to the width of each dry-type chemical analysis film, wherein the restriction means and the push member are capable of being coupled with each other with the urging means being compressed, and the coupling of the restriction means and the push member with each other is capable of being released by an external force after the restriction means and the push member in the coupled state have been located in the box housing.

The restriction means should preferably be engaged with inner wall surfaces of the box housing such that the restriction means can move and such that the position for restriction can be altered. Also, the restriction means may be constituted of a stopper having a stop portion, which comes into contact with part of the push member. Further, the urging means may restrict the distance of movement of the push member in the direction heading away from the take-out opening to at most a value equal to the width of each dry-type chemical analysis film when the urging means reaches the limit of deformation thereof without the restriction means.

With the cartridge for dry-type chemical analysis films in accordance with the present invention, in the initial state in which the dry-type chemical analysis films have been accommodated in the cartridge, the distance of movement of the push member in the direction heading away from the take-out opening is restricted to at most the value equal to the width of each dry-type chemical analysis film by the location of the restriction means. In cases where the cartridge falls and strikes against the floor, or the like, with the side of the take-out opening facing down, the push member will move in the direction, that compresses the dry-type chemical analysis films. However, in such cases, the push member can be returned to the original position and does not lock the dry-type chemical analysis films in the compressed state. Also, in cases where the cartridge falls and strikes against the floor, or the like, with the side opposite to the take-out opening facing down, the push member will move in the direction such that the dry-type chemical analysis films may be released from the pushing force. However, in such cases, the distance of movement of the push member can be restricted by the restriction means to at most the value equal to the width of each dry-type chemical analysis film. Therefore, there is no risk that the dry-type chemical analysis films become upright or are turned over. Further, after the cartridge has been subjected to the impact, by the effects of the urging force of the urging means, the push member is caused to push the dry-type chemical analysis films in the stacked state towards the take-out opening in the same manner as before. Accordingly, the dry-type chemical analysis films can be accurately taken out of the take-out opening one after another. Also, a measurement failure due to turn-over of the dry-type chemical analysis films does not occur.

The cartridge for dry-type chemical analysis films in accordance with the present invention may be constituted such that the restriction means and the push member can be coupled with each other with the urging means being compressed, and such that the coupling of the restriction means and the push member with each other can be released by an external force after the restriction means and the push member in the coupled state have been located in the box housing. In such cases, the cartridge for dry-type chemical analysis films in accordance with the present invention can be assembled very easily.

Also, as described above, the restriction means may be engaged with inner wall surfaces of the box housing such that the restriction means can move and such that the position for restriction can be altered. In such cases, it becomes possible to cope with alterations in the thickness and the number of the dry-type chemical analysis films accommodated in the cartridge. Further, even if the number of the dry-type chemical analysis films accommodated in the cartridge reduces as the dry-type chemical analysis films are taken out of the cartridge, the prevention of the dry-type chemical analysis films from turning over can be effected continuously.

DESCRIPTION OF THE PREFERRED EMBODIMENTS

The present invention will hereinbelow be described in further detail with reference to the accompanying drawings.

Figure 1:
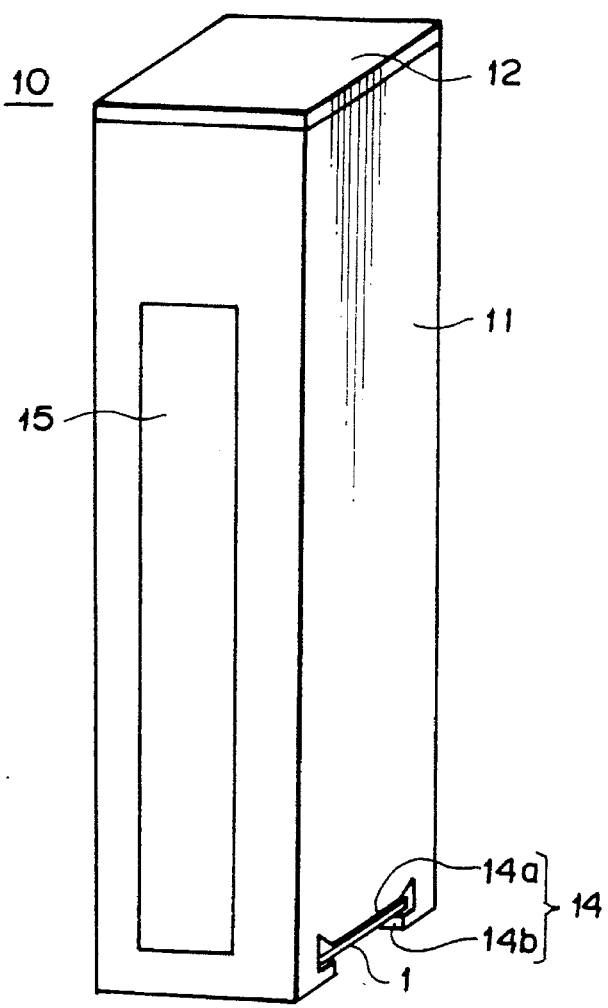
FIG. 1 is a perspective view showing an embodiment of the cartridge for dry-type chemical analysis films in accordance with the present invention.
Figure 2:
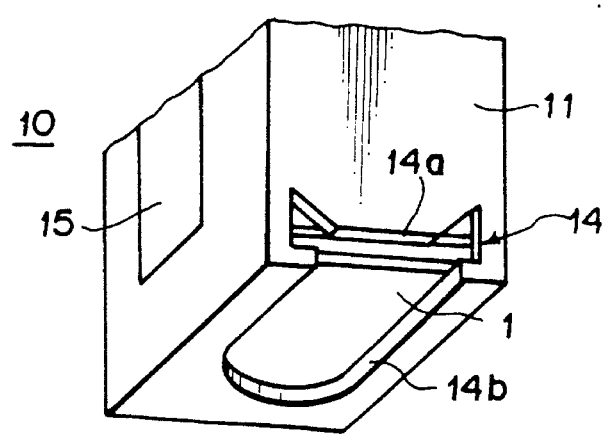
FIG. 2 is a perspective view showing a part around a take-out opening in the embodiment of FIG. 1.
Figure 3:
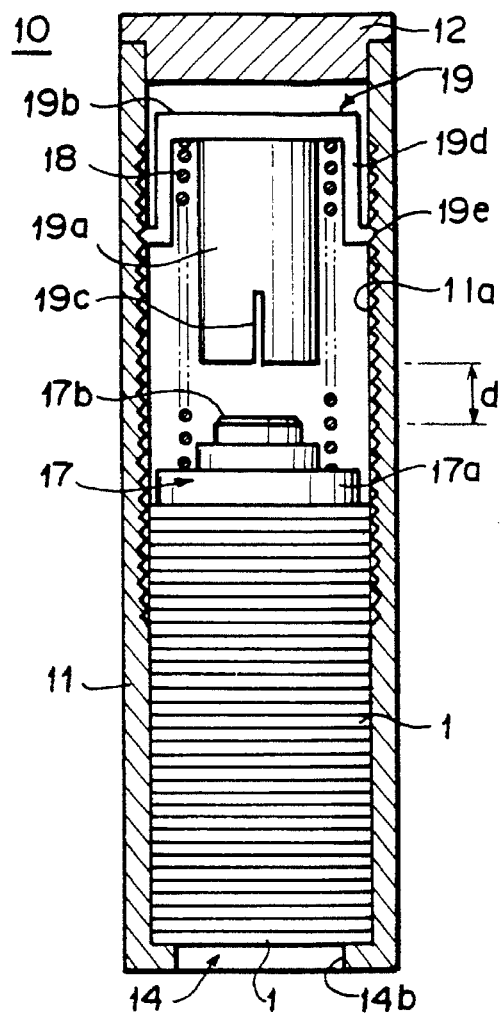
FIG. 3 is a vertical sectional view of the embodiment of FIG. 1.

FIG. 1 is a perspective view showing an embodiment of the cartridge for dry-type chemical analysis films in accordance with the present invention. FIG. 2 is a perspective view showing a part around a take-out opening in the embodiment of FIG. 1. FIG. 3 is a vertical sectional view of the embodiment of FIG. 1.

A cartridge 10 is provided with a square box housing 11, which accommodates therein a stack of a plurality of dry-type chemical analysis films 1, 1, . . . A feed-in opening, through which the dry-type chemical analysis films 1, 1, . . . are to be fed into the cartridge 10, is formed at one end (i.e., at the top end) of the box housing 11. The feed-in opening is covered with a cover member 12.

A take-out opening 14, through which the dry-type chemical analysis films 1, 1, . . . are to be taken out of the cartridge 10 one after another, is formed at the other end (i.e., at the bottom end) of the box housing 11. The take-out opening 14 is constituted of a first opening 14a, which is open to the side surface of the box housing 11 and through which a single dry-type chemical analysis film 1 can pass, and a second opening 14b, which is open to the bottom surface of the box housing 11 and into which a take-out suction cup (not shown) for sucking and holding the dry-type chemical analysis film 1 enters. Part of the lower end of the aforesaid side surface of the box housing 11 is cut away by the second opening 14b such that the first opening 14a and the second opening 14b may continue to each other.

The thickness of the dry-type chemical analysis film 1 accommodated in the cartridge 10 often varies for different specific biochemical substances to be analyzed. The size of the first opening 14a is adjusted in accordance with the thickness of the dry-type chemical analysis film 1 such that only a single dry-type chemical analysis film 1 can be reliably taken out through the take-out opening 14.

Magnetic stripes 15, which represent the characteristics of the dry-type chemical analysis films 1, 1, . . . accommodated in the cartridge 10, and the like, are put on an outer wall part of the other side surface of the box housing 11.

A push member 17 is located in the box housing 1 such that the push member 17 can slide. The push member 17 comes into contact with the stack of the dry-type chemical analysis films 1, 1, . . . from the side opposite to the take-out opening 14 and pushes the stack of the dry-type chemical analysis films 1, 1, . . . in the direction heading towards the take-out opening 14. Also, a coiled spring 18 is located in the box housing 11. The coiled spring 18 serves as an urging means, which urges the push member 17 in the direction heading towards the take-out opening 14. Further, a stopper 19 is located in the box housing 11 and is engaged with the inner walls of the box housing 11. The stopper 19 serves as a restriction means, which restricts the distance of movement of the push member 17 in the direction heading away from the take-out opening 14.

Figure 4:
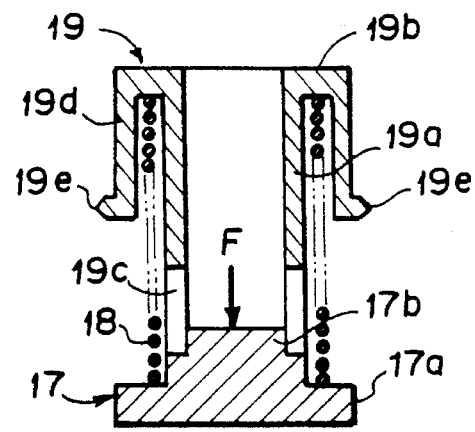
FIG. 4 is a sectional view showing a push member and a stopper coupled with each other.
Figure 5:
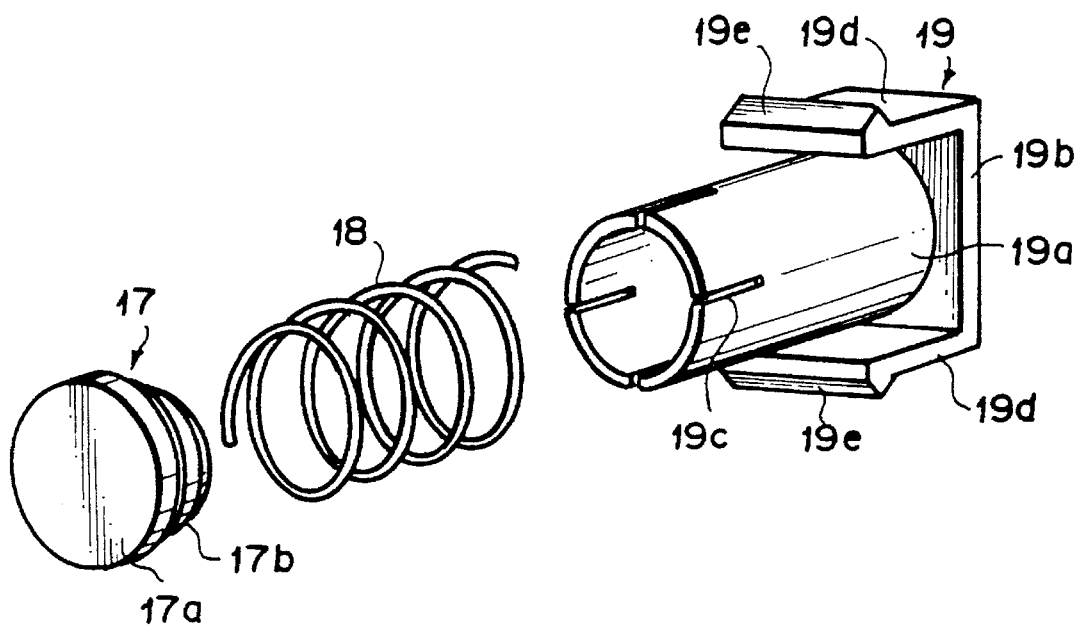
FIG. 5 is a developed perspective view showing the push member and the stopper.

The structures of the push member 17, the coiled spring 18, and the stopper 19 are also shown in FIGS. 4 and 5. The push member 17 comprises a main body 17a, which constitutes a pushing surface, and a step-like fitting portion 17b, which is formed at the back of the main body 17a. The stopper 19 comprises a cylindrical stop portion 19a, which extends axially, and a U-shaped base member 19b, which is secured to one end of the stop portion 19a. A plurality of axially extending slits 19c, 19c, . . . are formed at the other end of the stop portion 19a and impart resilience thereto. The fitting portion 17b of the push member 17 can be inserted into and fitted in the other end of the stop portion 19a. In this manner, as illustrated in FIG. 4, the push member 17 and the stopper 19 can be coupled with each other.

The position, at which the stopper 19 is engaged with the box housing 11, can be altered. Specifically, the base member 19b is provided with longitudinal pieces 19d, 19d, which can be deformed resiliently. Also, outwardly projecting claws 19e, 19e are formed at the ends of the longitudinal pieces 19d, 19d. Further, longitudinally extending ratchet teeth 11a, 11a are formed on inner wall surfaces of the box housing 11, which stand facing each other. The claws 19e, 19e of the stopper 19 engage with the ratchet teeth 11a, 11a.

One end of the coiled spring 18 is brought into contact with the back surface of the main body 17a on the side outward from the outer periphery of the fitting portion 17b of the push member 17. The other end of the coiled spring 18 is brought into contact with the back surface of the base member 19b on the side outward from the outer periphery of the cylindrical stop portion 19a of the stopper 19. In this state, the coiled spring 18 is contracted and fitted between the push member 17 and the stopper 19. As illustrated in FIG. 4, before the push member 17 and the stopper 19 are incorporated into the box housing 11, the fitting portion 17b of the push member 17 is coupled with the end of the stop portion 19a of the stopper 19 by the fitting force larger than the urging force of the coiled spring 18. In this manner, the push member 17 and the stopper 19 are coupled with each other as a unit with the coiled spring 18 being contracted between them.

The length and the spring constant of the coiled spring 18 are set in accordance with the length of the box housing 11 and the height of the stack of the dry-type chemical analysis films 1, 1, . . ., which are accommodated in the box housing 11, such that, even if the base member 19b of the stopper 19 is kept at the initial position without being moved, the last single dry-type chemical analysis film 1, which remains after all of the other dry-type chemical analysis films 1, 1, . . . have been taken out of the box housing 11, can be pushed by the push member 17.

FIG. 3 shows the initial state, in which a predetermined number of the dry-type chemical analysis films 1, 1, . . . have been accommodated in the box housing 11. In the initial state, the distance d, by which the push member 17 can retract in the direction heading away from the take-out opening 14 (i.e., the distance d between the position, at which the fitting portion 17b of the push member 17 is currently located, and the position, at which the fitting portion 17b comes into contact with the end of the stop portion 19a of the stopper 19) is set to be at most a value equal to the width of each dry-type chemical analysis film 1. Specifically, the distance d is set such that, even if the push member 17 moves in the direction heading away from the take-out opening 14, the dry-type chemical analysis films 1, 1, . . . may not become upright or may not be turned over. The setting of the distance d between the fitting portion 17b and the stop portion 19a can be carried out easily, for example, by putting graduations, or the like, on the outer wall of the box housing 11.

Figure 7A:
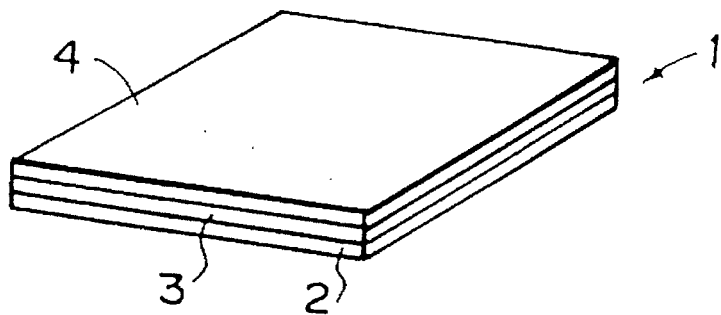
FIGS. 7A, 7B, and 7C are perspective views showing dry-type chemical analysis films.
Figure 7B:
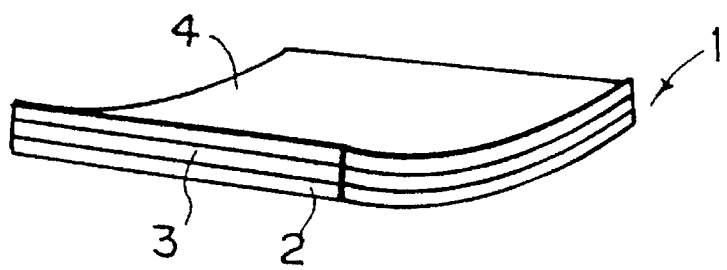
Figure 7C:
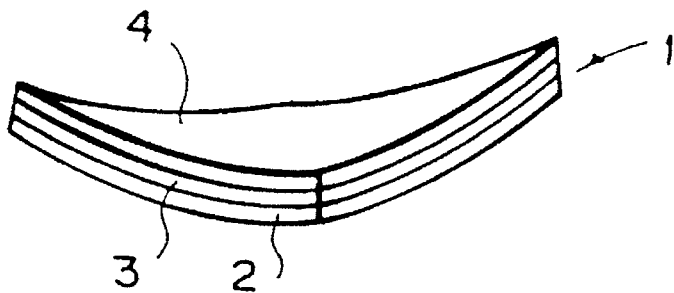

As illustrated in FIGS. 7A, 7B, and 7C, each of the dry-type chemical analysis films 1, 1, . . . accommodated in the cartridge 10 is constituted of a film piece (or a film chip) comprising a light transmitting substrate 2, which may be constituted of a plastic sheet, e.g., an organic polymer sheet, such as a polyethylene terephthalate (PET) sheet or a polystyrene sheet, and a reagent layer 3, which is overlaid on the substrate 2 with a coating process, an adhesion process, or the like. A spreading layer 4 is overlaid on the reagent layer 3 with a laminating process, or the like. The dry-type chemical analysis film 1 does not have the frames such as those of conventional chemical analysis slides.

The reagent layer 3 is constituted of at least a single layer, which comprises a hydrophilic polymer binder, such as gelatin, or a porous layer, and a detection reagent and a reagent necessary for a color reaction (a chemical analysis reagent or an immune analysis reagent) contained in the hydrophilic polymer binder or the porous layer. The detection reagent can react selectively with an analyte. The spreading layer 4 is constituted of a material, which is not affected by the rubbing with an external material, e.g. a woven fabric or a knitted fabric of a synthetic fiber, such as a polyester fiber; a woven fabric, a knitted fabric, or a nonwoven fabric of a blend of a natural fiber and a synthetic fiber; or paper. The spreading layer 4 thus serves as a protective layer. Also, the spreading layer spreads a liquid sample, which has been spotted onto the spreading layer 4, such that the liquid sample can be fed uniformly onto the reagent layer 3.

As illustrated in FIG. 7A, under the normal humidity condition, the dry-type chemical analysis film 1 has a flat plane-like shape. However, when the dry-type chemical analysis film 1 is stored, such that no chemical reaction may progress, the dry-type chemical analysis film 1 is placed under a dry environment (at humidity of, e.g., 20% or less). Therefore, in such cases, the dry-type chemical analysis film 1 becomes curved with the spreading layer 4 facing inwardly. Specifically, as illustrated in FIG. 7B, the dry-type chemical analysis film 1 becomes curved in one direction. Alternatively, as illustrated in FIG. 7C, the dry-type chemical analysis film 1 becomes curved in a plurality of directions.

The dry-type chemical analysis films 1, 1, . . . are loaded into the cartridge 10 in the manner described below. Specifically, for example, 100 or 50 sheets of dry-type chemical analysis films 1, 1, . . . are stacked such that the substrate 2 of each dry-type chemical analysis film 1 may face down. The dry-type chemical analysis films 1, 1, . . . are thereafter inserted into the box housing 11 through the opening, from which the cover member 12 has been removed. At this time, a slight space is formed between the adjacent dry-type chemical analysis films 1, 1 due to their curved shapes. As a whole, the dry-type chemical analysis films 1, 1, . . . have resilience in the direction, along which they are compressed.

As illustrated in FIG. 4, the push member 17 and the stopper 19 are fitted to each other as a unit with the coiled spring 18 being contracted between them. The unit is then inserted into the box housing 11. The claws 19e, 19e of the stopper 19 are pushed into the box housing 11 while they are being successively engaged with the ratchet teeth 11a, 11a. When or before the push member 17 comes into contact with the stack of the dry-type chemical analysis films 1, 1, . . ., an external force F is applied to push the push member 17 through the internal hole of the cylindrical stop portion 19a of the stopper 19, and the stopper 19 and the fitting portion 17b of the push member 17 are thereby disengaged from each other. Thereafter, the cover member 12 is fitted to the box housing 11. In this initial state, as illustrated in FIG. 3, the distance d is set to be at most a value equal to the width of each dry-type chemical analysis film 1, and the coiled spring 18 pushes the stack of the dry-type chemical analysis films 1, 1, . . . via the push member 17.

As described above, the push member 17 and the stopper 19 are fitted to each other as a unit, and the coiled spring 18 is contracted and secured between them. Therefore, the unit is easy to process, and the cartridge 10 can be processed and assembled easily. The fitting force between the stopper 19 and the push member 17 is set to be larger than the urging force of the coiled spring 18 and smaller than the force of engagement between the claws 19e, 19e and the ratchet teeth 11a, 11a.

In the aforesaid initial state, in which the predetermined number of the dry-type chemical analysis films 1, 1, . . . have been accommodated in the box housing 11, the cartridge 10 is conveyed or processed so as to be loaded into a supplier of a biochemical analysis system, or the like. In such cases, it may occur by mistake that the cartridge 10 falls and strikes against the floor, or the like. In cases where the cartridge 10 falls and strikes against the floor, or the like, with the side of the take-out opening 14 facing down, the push member 17 will move in the direction, that compresses the dry-type chemical analysis films 1, 1, . . ., due to the impact. However, in such cases, the push member 17 can be returned to the original position by the resilience of the dry-type chemical analysis films 1, 1, . . . and does not lock the dry-type chemical analysis films 1, 1, . . . Also, even if the impact given to the cartridge 10 is large, the position of engagement of the claws 19e, 19e with the ratchet teeth 11a, 11a does not shift.

Also, in cases where the cartridge 10 falls and strikes against the floor, or the like, with the side opposite to the take-out opening 14 facing down, the push member 17 will move in the direction heading towards the stopper 19 due to the impact such that the dry-type chemical analysis films 1, 1, . . . may be released from the pushing force. However, in such cases, the movement of the push member 17 is restricted by the end of the stopper 19 coming into contact with the push member 17. Even if the push member 17 moves the maximum possible distance, i.e. the distance d, a large space is not formed around each dry-type chemical analysis film 1. Therefore, there is no risk that the dry-type chemical analysis films 1, 1, . . . become upright or are turned over. Further, after the cartridge 10 has been subjected to the impact, by the effects of the urging force of the coiled spring 18, the push member 17 is caused to push the dry-type chemical analysis films 1, 1, . . . in the stacked state towards the take-out opening 14 in the same manner as before.

In cases where the cartridge 10, from which some of the dry-type chemical analysis films 1, 1, . . . have been taken out, is taken out of the supplier of the biochemical analysis system, or the like, for the purposes of troubleshooting, or the like, during the use of the cartridge 10, if the stopper 19 is set at the initial position for restriction shown in FIG. 3, the push member 17 will be located at a position lower than its initial position as the number of the dry-type chemical analysis films 1, 1, . . . decreases, and the distance d between the push member 17 and the end of the stopper 19 will become larger than the width of each dry-type chemical analysis film 1. In such cases, the stopper 19 is pushed down towards the push member 17, and the position of engagement of the claws 19e, 19e with the ratchet teeth 11a, 11a is altered. In this manner, the distance d is again set to be at most the value equal to the width of each dry-type chemical analysis film 1. The same functions as those described above can thus be obtained.

In cases where the thickness of each dry-type chemical analysis film 1 varies or the number of the dry-type chemical analysis films 1, 1, . . . accommodated in the cartridge 10 varies in the initial state, the position of engagement of the claws 19e, 19e with the ratchet teeth 11a, 11a is altered in accordance with the height of the entire stack of the dry-type chemical analysis films 1, 1, . . . accommodated in the cartridge 10.

Figure 6:
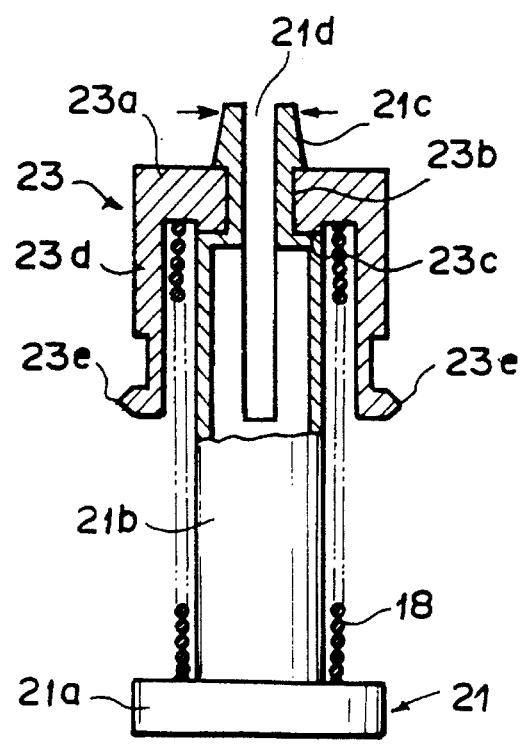
FIG. 6 is a sectional view showing a push member and a stopper coupled with each other in a different embodiment of the cartridge for dry-type chemical analysis films in accordance with the present invention.

FIG. 6 is a sectional view showing a push member 21 and a stopper 23 serving as a restriction means, which are coupled with each other and which are employed in a different embodiment of the cartridge for dry-type chemical analysis films in accordance with the present invention. The push member 21 and the stopper 23 are located in the same box housing 11 as that in the aforesaid embodiment.

In the embodiment of FIG. 6, the push member 21 comprises a main body 21a, which constitutes a pushing surface, and a cylindrical protrusion 21b, which extends axially from the back surface of the main body 21a. A fitting portion 21c is formed at the end of the protrusion 21b. A step-like engagement portion is formed on the upper end side of the small diameter neck of the fitting portion 21c. Also, a slit-like longitudinal groove 21d extends axially from the upper end of the fitting portion 21c, and the fitting portion 21c is thereby imparted with resilience.

The stopper 23 comprises a U-shaped base member 23a having an engagement hole 23b, which is formed at the center portion of the base member 23a. The fitting portion 21c at the end of the protrusion 21b of the push member 21 can be inserted into the engagement hole 23b. The peripheral end face of the engagement hole 23b is constituted as a stop portion 23c, which comes into contact with the end of the protrusion 21b of the push member 21 and restricts the movement of the push member 21.

As in the aforesaid embodiment, the stopper 23 comprises a base member 23a provided with longitudinal pieces 23d, 23d, and claws 23e, 23e are respectively formed at the ends of the longitudinal pieces 23d, 23d. The claws 23e, 23e are engaged with the ratchet teeth 11a, 11a, which are formed on the inner wall surfaces of the box housing 11 standing facing each other and which are shown in FIG. 3. Also, the position of engagement of the claws 23e, 23e with the box housing 11 can be altered.

The coiled spring 18 serving as the urging means is constituted in the same manner as that in the aforesaid embodiment. One end of the coiled spring 18 is brought into contact with the back surface of the main body 21a on the side outward from the outer periphery of the protrusion 21b of the push member 21. The other end of the coiled spring 18 is brought into contact with the back surface of the base member 23b. In this state, the coiled spring 18 is contracted and fitted between the push member 21 and the stopper 23. The fitting portion 21c at the end of the protrusion 21b of the push member 21 is inserted and fitted into the engagement hole 23b of the stopper 23. In this manner, the push member 21 and the stopper 23 are coupled with each other as a unit with the coiled spring 18 being contracted between them.

The unit is then inserted into the box housing 11. The claws 23e, 23e of the stopper 23 are engaged with the ratchet teeth 11a, 11a, and the stopper 23 is thereby releasably secured to the box housing 11. Thereafter, an external force is applied to the end of the fitting portion 21c so as to narrow the longitudinal groove 21d. In this manner, the fitting portion 21c is disengaged and removed from the engagement hole 23b of the stopper, and the push member 21 is thus separated from the stopper 23. As a result, the push member 21 is urged by the coiled spring 18 to push the stack of the dry-type chemical analysis films 1, 1, . . . in the direction heading towards the take-out opening 14.

In the cartridge 10 in which the push member 21 and the stopper 23 are incorporated, the function for preventing the dry-type chemical analysis films 1, 1, . . . from turning over due to impact can be obtained in the same manner as that in the aforesaid embodiment. When the push member 21 is retracted in the direction heading away from the take-out opening 14 due to impact, the end of the protrusion 21b comes into contact with the stop portion 23c, which is constituted by the end face of the stopper 23, and further movement of the push member 21 is thereby restricted.

With the embodiments described above, the stopper 19 or 23 is located in the box housing 11 such that the position of engagement of the stopper 19 or 23 with the box housing 11 can be altered. Therefore, it becomes possible to cope with a change in the thickness of each dry-type chemical analysis film 1 and a change in the number of the dry-type chemical analysis films 1, 1, . . . accommodated in the cartridge 10. Also, the position of the stopper 19 or 23 for restriction of the movement of the push member 17 or 21 can be altered in accordance with the decrease in the number of the dry-type chemical analysis films 1, 1, . . . accommodated in the cartridge 10. However, as for a cartridge 10, in which a predetermined number of the dry-type chemical analysis films 1, 1, . . . having a predetermined thickness are always accommodated and there is no risk that the cartridge 10 falls during the use, the position of engagement of the stopper 19 or 23, i.e. the position for restriction, need not necessarily be altered. Therefore, in such cases, the cartridge 10 may be constituted such that the stopper 19 or 23 is secured to a specific single position. Also, the cover member 12 may serve as the stopper. In such cases, the stopper 19 or 23 may be constituted such that it can be temporarily coupled with the push member 17 or 21 as a unit with the coiled spring 18 being contracted between them and such that the unit can be processed easily during the assembling of the cartridge 10, or the like.

As for the structure for the coupling of the stopper 19 or 23 with the push member 17 or 21, it is also possible to employ a threaded structure, a bayonet structure, or the like.

In the embodiments described above, the restriction of the distance of movement of the push member 17 or 21 is effected by the provision of the stop portion 19a or 23c, which comes into contact with part of the push member 17 or 21 when the push member 17 or 21 moves. Alternatively, the restriction of the distance of movement of the push member 17 or 21 may be effected by the urging means when the urging means reaches the limit of deformation thereof without the restriction means.

Specifically, in cases where the urging means is constituted of the coiled spring 18, when the coiled spring 18 is compressed to the maximum extent, the adjacent coil portions come into contact with each other, and the coiled spring 18 cannot be compressed any more. Such characteristics may be utilized. More specifically, the characteristics of the coiled spring 18 may be set such that the movement of the push member 17 or 21 can be restricted at the position, at which the limit of deformation of the coiled spring 18 is reached when the push member 17 or 21 moves due to impact.

In the embodiments described above, the dry-type frameless chemical analysis film pieces are accommodated as the dry-type chemical analysis films 1, 1, . . . in the cartridge 10. The cartridge for dry-type chemical analysis films in accordance with the present invention can also be applied to dry-type chemical analysis films, which take on the form of slides having frames, filter paper type of dry-type chemical analysis films, or the like.

What is claimed is:

1. A cartridge for dry-type chemical analysis films, comprising:

i) a box housing, which accommodates therein a stack of a plurality of dry-type chemical analysis films and which has a take-out opening at one end such that the dry-type chemical analysis films may be taken out of the box housing through the take-out opening one after another, each of said dry-type chemical analysis films having a preset width, ii) a push member, which is located in the box housing so as to be capable of sliding, and which comes into contact with the stack of the plurality of the dry-type chemical analysis films from the side opposite to the take-out opening and pushes the stack of the plurality of the dry-type chemical analysis films in the direction heading towards the take-out opening, iii) an urging means, which is located in the box housing and which urges the push member in the direction heading towards the take-out opening, and iv) a restriction means comprising a stopper having a stop portion which comes into contact with part of the push member, said stopper being located in the box housing and restricting the distance of movement of the push member in the direction heading away from the take-out opening to at most a value equal to the preset width of each dry-type chemical analysis film.

2. A cartridge for dry-type chemical analysis films, comprising:

i) a box housing, which accommodates therein a stack of a plurality of dry-type chemical analysis films and which has a take-out opening at one end such that the dry-type chemical analysis films may be taken out of the box housing through the take-out opening one after another, each of said dry-type chemical analysis films having a preset width, ii) a push member, which is located in the box housing so as to be capable of sliding, and which comes into contact with the stack of the plurality of the dry-type chemical analysis films from the side opposite to the take-out opening and pushes the stack of the plurality of the dry-type chemical analysis films in the direction heading towards the take-out opening, iii) an urging means, which is located in the box housing and which urges the push member in the direction heading towards the take-out opening, and iv) a restriction means, which is located in the box housing and which restricts the distance of movement of the push member in the direction heading away from the take-out opening to at most a value equal to the preset width of each dry-type chemical analysis film, wherein the restriction means and the push member are capable of being coupled with each other with the urging means being compressed, and the coupling of the restriction means and the push member with each other is capable of being released by an external force after the restriction means and the push member in the coupled state have been located in the box housing.

3. A cartridge as defined in claim 2 wherein the restriction means is engaged with inner wall surfaces of the box housing such that the restriction means can move and such that the position for restriction can be altered.

4. A cartridge as defined in claim 3 wherein the restriction means is constituted of a stopper having a stop portion, which comes into contact with part of the push member.

* * * * *